United States Patent
Wu

(10) Patent No.: US 9,856,045 B2
(45) Date of Patent: Jan. 2, 2018

(54) SYSTEM AND METHOD FOR MANUFACTURING AN E-BEAM STERILIZED FLEXBLE BAG

(71) Applicant: AESCULAP IMPLANT SYSTEMS, LLC, Center Valley, PA (US)

(72) Inventor: Nicholas Wu, Irvine, CA (US)

(73) Assignee: AESCULAP IMPLANT SYSTEMS, LLC, Center Valley, PA (US)

( * ) Notice: Subject to any disclaimer, the term of this patent is extended or adjusted under 35 U.S.C. 154(b) by 569 days.

(21) Appl. No.: 14/475,275

(22) Filed: Sep. 2, 2014

(65) Prior Publication Data

US 2015/0059288 A1  Mar. 5, 2015

Related U.S. Application Data

(60) Provisional application No. 61/872,833, filed on Sep. 2, 2013.

(51) Int. Cl.

| | |
|---|---|
| B65B 55/02 | (2006.01) |
| A61L 2/08 | (2006.01) |
| B65B 3/02 | (2006.01) |
| B65B 29/10 | (2006.01) |
| B65B 55/08 | (2006.01) |
| B65B 55/10 | (2006.01) |
| B65B 3/00 | (2006.01) |
| B65B 31/02 | (2006.01) |
| B65B 57/04 | (2006.01) |
| B65B 57/06 | (2006.01) |

(Continued)

(52) U.S. Cl.
CPC ............ *B65B 55/027* (2013.01); *A61L 2/087* (2013.01); *B65B 3/003* (2013.01); *B65B 3/02* (2013.01); *B65B 29/10* (2013.01); *B65B 31/024* (2013.01); *B65B 55/08* (2013.01); *B65B 55/10* (2013.01); *B65B 57/04* (2013.01); *B65B 57/06* (2013.01); *B65B 57/08* (2013.01); *B65B 57/18* (2013.01); *B65B 2220/14* (2013.01)

(58) Field of Classification Search
CPC ..... B65B 55/025; B65B 55/027; B65B 55/08; B65B 29/10; B65B 31/024; B65B 43/60; B65B 2220/14; A61L 2/087
See application file for complete search history.

(56) References Cited

U.S. PATENT DOCUMENTS 3,674,422 A * 7/1972 Gray ........................ B65B 55/16
                                                              219/700
3,676,058 A * 7/1972 Gray ........................ B65B 55/16
                                                              131/299

(Continued)

FOREIGN PATENT DOCUMENTS

| DE | 3231514 A1 * | 1/1984 | ........... B65B 31/024 |
| EP | 1245493 A1 * | 10/2002 | ........... B65B 55/027 |

(Continued)

*Primary Examiner* — Stephen F Gerrity
(74) *Attorney, Agent, or Firm* — Kenealy Vaidya LLP

(57) ABSTRACT

A flexible container, system and method of manufacture can include an in-line system that allows flexible containers of varying sizes to be manufactured in a single relatively high speed and efficient production line and in a single clean room through the use of transport and exchange equipment configured to adeptly handle flexible containers throughout the process.

21 Claims, 7 Drawing Sheets

(51) Int. Cl.
*B65B 57/08* (2006.01)
*B65B 57/18* (2006.01)

(56) References Cited

U.S. PATENT DOCUMENTS

| | | | | |
|---|---|---|---|---|
| 4,598,529 | A * | 7/1986 | Pongrass et al. | B65B 55/08 53/384.1 |
| 5,115,626 | A * | 5/1992 | Rutter et al. | B65B 55/027 53/284.7 |
| 5,520,975 | A * | 5/1996 | Inoue et al. | A61J 1/2093 424/443 |
| 5,871,477 | A * | 2/1999 | Isono et al. | A61J 1/2093 206/219 |
| 5,944,709 | A * | 8/1999 | Barney et al. | B65B 55/16 206/219 |
| 6,364,864 | B1 * | 4/2002 | Mohiuddin et al. | A61J 1/10 206/219 |
| 6,468,377 | B1 * | 10/2002 | Sperko et al. | B65B 55/16 156/146 |
| 7,111,649 | B2 * | 9/2006 | Py | B65B 55/025 141/11 |
| 2001/0039977 | A1 * | 11/2001 | Sharon et al. | B65B 29/10 141/1 |
| 2008/0051937 | A1 * | 2/2008 | Khan et al. | B65B 3/003 700/240 |
| 2009/0134338 | A1 * | 5/2009 | Eguchi et al. | B65B 55/08 250/396 R |
| 2010/0132307 | A1 * | 6/2010 | Nishino et al. | B65B 55/08 53/167 |
| 2010/0189831 | A1 * | 7/2010 | Fonte-Ruiz | B65B 55/10 425/66 |
| 2010/0270477 | A1 * | 10/2010 | Nishino et al. | B65B 55/08 250/455.11 |
| 2011/0006225 | A1 * | 1/2011 | Fletcher et al. | A61L 2/087 250/492.3 |
| 2013/0108189 | A1 * | 5/2013 | Lejeune et al. | B65B 55/08 383/41 |
| 2014/0158500 | A1 * | 6/2014 | Voth et al. | B65B 55/08 198/617 |
| 2015/0203222 | A1 * | 7/2015 | Zonato | B65B 55/10 53/455 |

FOREIGN PATENT DOCUMENTS

| | | | | |
|---|---|---|---|---|
| GB | 1525484 | A * | 9/1978 | B65B 55/08 |
| GB | 2507607 | A * | 5/2014 | B65B 55/08 |
| JP | 2003072717 | A * | 3/2003 | |
| WO | WO 2005120960 | A1 * | 12/2005 | B65B 55/025 |
| WO | WO 2012055459 | A1 * | 5/2012 | B65B 55/022 |
| WO | WO 2014188153 | A1 * | 11/2014 | B65B 55/08 |

* cited by examiner

SYSTEM AND METHOD FOR MANUFACTURING AN E-BEAM STERILIZED FLEXBLE BAG

This application claims priority under 35 U.S.C. §119(e) to U.S. Provisional Application No. 61/872,833, filed on Sep. 2, 2013, the disclosure of which is incorporated herein by reference in its entirety.

BACKGROUND

1. Field

The presently disclosed subject matter relates to systems and methods for manufacturing a flexible container for the storage and administration of fluids and solutions, and more particularly, to systems and methods providing a fully integrated continuous system and method for aseptically forming, filling, sealing and packaging flexible and sterile containers for storing and administering intravenous (IV) materials, such as medical or pharmaceutical liquids, powders, gases or solutions.

2. Discussion of Related Art

Various medical solutions are commonly administered intravenously (via IV) from sterile containers to patients. These solutions may include any medical type fluids, such as replacement body fluids and even solutions containing a medicament (drug). Common packaging for the storage and administration of these solutions includes flexible containers having a compartment for storing the solution. An outlet port is coupled to the compartment for administration and delivery of the solution to the patient through a standard IV arrangement.

Flexible containers manufactured under conventional processes typically require a multi-step manufacturing process in which the empty containers are formed, then sterilized separately offline, and then returned online for completion of the filling and finishing processes. Such a de-coupled approach creates material waste and process inefficiencies which results in a higher cost and increased manufacturing time, as well as increased risk of potential contamination or otherwise compromising the integrity of the container or the contents thereof.

SUMMARY

The disclosed embodiments describe a fully integrated system and method for aseptically forming, filling, sealing and packaging a flexible container that is provided for the storage and administration of IV materials, such as medical solutions. In one embodiment, the container is formed from a single planar sheet of a polymeric, possibly laminated, material in which the sheet is folded to define the front and rear surfaces or sides thereof. The volume enclosure is constructed of materials having high oxygen and moisture barrier properties which allows the thermoplastic container to be stored for extended periods of time without degrading the contents of the container. The volume enclosure can then be inflated with a pressurized gas or fluid to permanently stretch the front and/or rear sheets outwardly and to thereby increase the volume capacity of the container. In another embodiment, the container incorporates a transparent front sheet made from a planar layer of a polymeric and possibly laminated material and an opposing rear sheet. The rear sheet is made from a similar or identical planar layer of polymeric material(s). The front and rear sheets are sealed together along a common peripheral edge to form a volume enclosure. Yet, another alternative embodiment of the container incorporates multiple compartments, separated by peelable seals, for containing a diluent and at least one medicament. The peelable seals are ruptured by manipulation of the container to thereby mix the contents, i.e., the diluent and medicament(s), together for delivery through a conventional IV set to a patient.

The disclosed embodiments also describe a system for manufacturing a flexible bag, that includes a single contained environment 100 configured for aseptic processing (same single aseptic environment enclosure 101), a flexible bag manufacturing station configured to manufacture a flexible bag and located within the contained environment, an e-beam sterilization station configured to sterilize the flexible bag and located within the single contained environment; and a fill station configured to fill the flexible bag with at least two different materials, the fill station located within the single contained environment.

BRIEF DESCRIPTION OF THE DRAWINGS

The disclosed subject matter of the present application will now be described in more detail with reference to exemplary embodiments of the apparatus, system, and method, given by way of example, and with reference to the accompanying drawings, in which.

DETAILED DESCRIPTION OF EXEMPLARY EMBODIMENTS

Figure 1:
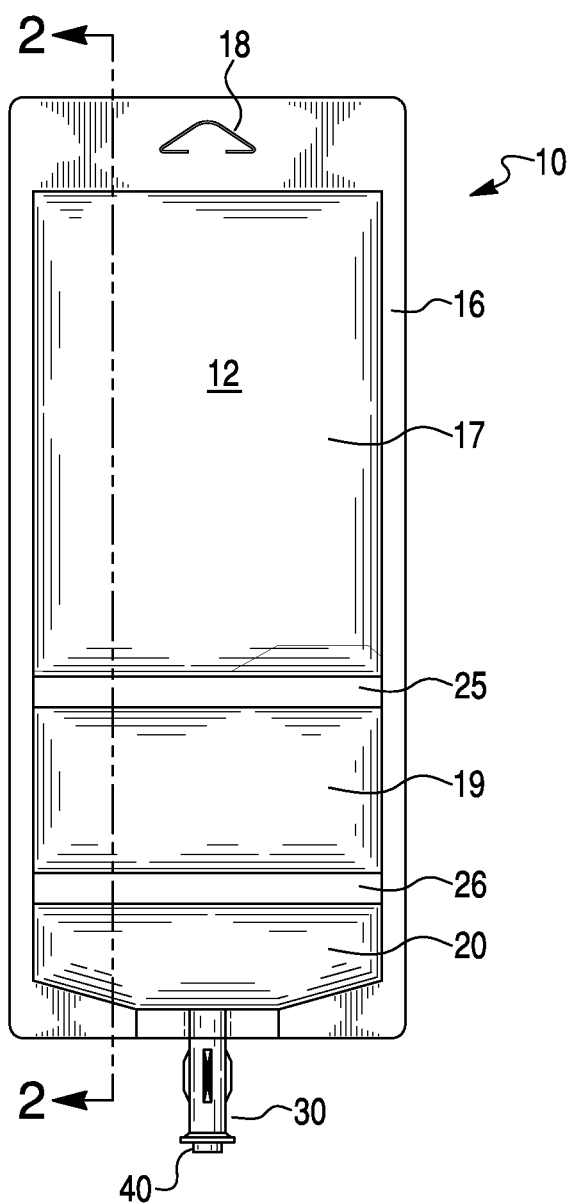
FIG. 1 is a front view of a flexible container made in accordance with principles of the disclosed subject matter.

As described above, the disclosed subject matter provides systems and methods for manufacturing a flexible container for the storage and administration of materials such as medical solutions. The definition of a flexible container may include, but is not limited to, a flexible bag that is not configured to maintain its own shape under the force of normal gravity, a conventional IV bag, a medicament solution bag, and any of the containers described in commonly assigned U.S. Pat. Nos. 5,944,709; 6,198,106; 6,165,161; 6,203,535; 5,910,138; 5,928,213; 6,468,377; 6,117,123; 6,846,305; 6,764,567; and 6,966,951, which are hereby incorporated in their entirety by reference. Whereas the containers described throughout the instant application will be described as flexible containers or bags, it is also within the scope of the disclosed subject matter for the containers to include any container capable of containing a fluid, a solid, gelatinous substance, powders, gaseous substances, and liquids, whether or not intended for consumption or use by humans and animals alike.

The flexible container can be segmented or partitioned into a plurality, e.g., two, three or more, chambers separated by at least one peelable seal. As described in the aforementioned United States patents, the peelable seals are rupturable so as to facilitate the mixing of the contents between the various chambers. For example, rupturing a peelable seal could allow the contents of the chambers to safely mix without exposure to the environment or being contacted by humans. A chamber can be larger than the other chamber(s) or each chamber can be of equal or substantially similar dimensions or volume. A first chamber, which can be the larger chamber, can contain a liquid diluent(s) while the other chamber(s) can contain an active pharmaceutical ingredient (API) and/or medicament, which can be either a dry powder or liquid. Another chamber can be empty and define or form a buffer space or region that separates the drug from a delivery set port.

Upon rupturing a primary peelable seal, the contents of the API containing chamber are mixed with the solution in the diluent chamber. After complete mixing has occurred, a secondary peelable seal can be ruptured and the mixed solution delivered to a patient or other target recipient via the delivery set port. The rupturing threshold of the primary peelable seal can be less or lower than the rupturing threshold of the secondary peelable seal, such that the primary peelable seal will rupture before the secondary peelable seal, thereby enabling the contents of the API and diluents containing chambers to be mixed before passing through the buffer chamber and through the delivery set port. The design of the container prohibits or at least substantially prevents delivery of any solution or dry powder through the delivery set port until the entire contents of the container have been thoroughly mixed, thereby reducing medication errors associated with separately compounding a drug with diluents. Additionally, the disclosed method of manufacturing the flexible bags eliminates a separate transfer process during manufacture and filling of the flexible bags that required additional structures and time requirements to maintain aseptic conditions, as well as added risk of contamination. Elimination of any process that has a potential of exposure to environmental (and possibly contaminated) conditions is desired when compounding drug mixtures within a pharmacy environment. The present process for manufacturing the flexible bags can be conducted entirely within the same controlled atmosphere, without requiring control of the environment of separate transfer containers between portions of the process.

The flexible containers can be formed from a clear and flexible plastic film with an optional barrier layer covering the API chamber. The barrier layer can be aluminum foil laminate or an otherwise opaque laminate or material. The optional barrier layer can provide a barrier against light, oxygen and moisture that might otherwise negatively impact the drug substance contained in the API chamber.

The disclosed process provides increased flexibility in container size, including increased volumes of the API and diluent chambers, while also reducing manufacturing time and costs. As a reference point, we note that the flexible containers described in the aforementioned patents can provide a diluent chamber containing 50 mL of diluent and an API chamber containing up to 4.0 g of a powdered drug or API.

The disclosed process for manufacturing flexible containers allows for increased container size, larger chamber volumes, such as, for example only, a diluent chamber, which may contain, for example, 250 mL or more of a diluent, and a larger range of API weight/volume, such as 8.0 g, or more. It should be noted that the API chamber formed by the disclosed process can contain various types or forms of API, such as liquid, gel, powder, capsules, granules, etc. The larger flexible containers which can be formed from the disclosed process accommodate a fill volume of the diluent chamber and a fill volume/weight of the API chamber for additional types of drugs that are not possible under the conventionally manufactured, smaller containers. The disclosed manufacturing process can continuously handle containers as a pouch via openings defined in the top and bottom ends of the pouch. The flexible containers can be continuously formed, sterilized, filled, and sealed in a fully integrated aseptic manufacturing process which can reduce process waste and manufacturing cost while more easily ensuring aseptic conditions.

The disclosed embodiments of the flexible container contemplate the use of a variety of materials capable of providing a robust seal, as well as the ability to protect the final product over the expected shelf life. Primary film material(s) include various polymeric materials, including, but not limited to, PET 60/40 6 mil, Excel 80/20 8 mil, PET/SiOx/80/20 6 mil, PET/80/20 6 mil, combinations thereof, etc. In some embodiments, a silicon oxide (SiOx) barrier can be added to the film structure.

In conventional flexible carriers, an aluminum foil barrier layer is provided on the back or rear surface as a barrier to light for the diluents and API chambers, and on the front surface as a barrier to light, possibly for the API chamber only. In an embodiment of the flexible container manufactured by the disclosed process, the aluminum foil barrier can be provided to both sides or surfaces of the API chamber to provide the needed barriers to moisture, oxygen and light for the active ingredients contained therein. Moreover, the aluminum barrier on the front side or surface of the flexible container can be peelable so as to provide an opportunity for visual inspection of the contents of the API chamber for visual defects prior to and/or during activation and use.

The disclosed flexible container can include a setport having a 80/20 PP/Kraton material composition. This composition prevents damage that can be caused by excessive spike insertion forces. This material also eliminates the need to use a mandrel to support the setport during the welding process. The disclosed process for filling the flexible container process is not amenable to the use of a mandrel during the sealing process because it is advantageous for the setport to independently maintain its shape during the sealing process. The use of the 80/20 PP/Kraton blend provides a harder finished product which allows the setport to maintain its shape under pressure but facilitates an acceptable spike insertion force.

The disclosed subject matter also includes embodiments that provide for a post-aseptic print and apply process that includes using preprinted label stock that can accommodate, for example, eight colors per label. The labels can be preprinted with the standard product information as desired. Variable data such as human readable and encoded lot numbers and expiration dates can be printed directly onto the preprinted labels using a black TTR print head, for example. The encoded data can include both 1-D and 2-D bar code formats.

The flexible container manufactured in accordance with the disclosed embodiments also maintains the integrity of the primary peelable seal which separates the diluent chamber from the API chamber until the point of use. In order to ensure the peelable seal remains intact during shipping and normal handling processes, the flexible container can be folded along the primary peelable seal and secured. In order to maintain the folded configuration for the flexible container, a secondary pressure sensitive stick-on tape can be applied to the flexible container. The stick-on tape secures the flexible container in the folded configuration and still allows for the end user to unfold the container at time of use.

The disclosed flexible container system allows for the production of a variety of container sizes, including but not limited to containers having diluent fill volumes of 50 mL, 100 mL, 250 mL, and 500 mL or more, for example.

The disclosed flexible container can include primary and secondary peelable seals that can separate the diluents chamber, the API chamber, and the forward buffer chamber of the container prior to activation. In one embodiment, the peelable seal width can be from about 4.0 mm to about 10.0 mm or more. In another embodiment, the peelable seal width is about 7.0 mm.

The disclosed flexible containers are configured for shipping in a manner that protects the flexible containers throughout the expected shipping conditions. A variety of corrugated case structures can be used to contain the flexible containers, including but not limited to a 250 mL corrugate case that is intended to hold 24 containers per case. In one embodiment, a wax layer is added to the corrugate. This wax layer minimizes abrasions on the primary container and corrugate dusting during expected shipping conditions. A center H-divider can optionally be added to the cases for structure.

Figure 2:
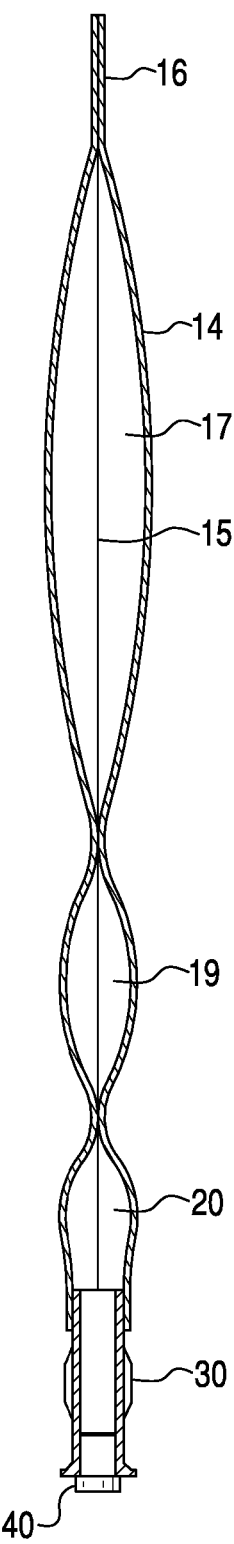
FIG. 2 is a side view of a flexible container made in accordance with principles of the disclosed subject matter.

FIGS. 1 and 2 show an exemplary flexible container that can be manufactured through the exemplary systems and methods described herein. Referring to FIGS. 1 and 2, an exemplary container 10 is shown that is made in accordance with the disclosed subject matter. Although the container 10 can be viewed in any orientation, for purposes of explanation, the position of the compartments of the container relative to one another are described with reference to the orientation of FIG. 1 which shows a front view of the flexible container, and FIG. 2 which shows a side cross-sectional view taken along the line 2-2 of the flexible container of FIG. 1. The container 10 can be formed from a generally planar front sheet 12 and an opposing generally planar back or rear sheet 14 (shown only in FIG. 2). The front and rear sheets 12 and 14 can be constructed of a single layer of flexible material or multi-layer laminates of flexible material.

The sheets 12 and 14 forming the container 10 can be provided separately and disposed opposing each other along a common plane 15 (FIG. 2). The sheets 12 and 14 are then sealed together along a common peripheral edge 16 with a permanent seal. The sealed common peripheral edge 16 extends around the entire periphery of the container 10 to form a first chamber 17. The peripheral seal may vary in configuration and width. An opening 18 can be provided on a top surface of the container 10 that allows the container to be mounted, hung from, or otherwise attached to, for example, a support stand. Alternatively, the front and rear sheets 12 and 14 may be formed from a single film sheet which is folded-over and the edges sealed together by any known or later developed sealing process.

In the exemplary embodiment of FIGS. 1 and 2, the container 10 is partitioned into three separate chambers: a first or upper chamber 17, a second or intermediate chamber 19 and a third or lower chamber 20, each of which can be sterile, depending on the intended application of the container 10. The upper and intermediate chambers 17 and 19 are separated from one another by a first peelable seal 25, while the intermediate and lower chambers 19 and 20 are separated from one another by a second peelable seal 26. In other embodiments of the disclosed subject matter, a peelable seal can only be provided between the upper chamber 17 and the intermediate chamber 19. In these embodiments, the seal between the intermediate chamber 19 and the lower chamber 20 can be rupturable through the application of a hydraulic force caused by a user forcing the contents of the upper and intermediate chambers 17 and 19 into the lower chamber 20.

A "peelable" seal, as the term is used herein, is a seal which is sufficiently durable to allow normal handling of the container without the seals rupturing and the contents of the compartments mixing unintentionally, yet which will rupture easily upon specific manipulation, allowing separation of the front sheet from the back sheet in the region of the seal, under hydraulic pressure applied by manipulating the container, thereby allowing mixing and dispensing of the container contents. A peelable seal can be formed by partially melting together the polymeric material present in the adjoining interior faces of the front and back sheets. The seal is obtained by, for example, a heat sealing process wherein heat and pressure is applied to a localized area with varying times, temperatures, and pressures which will be described in greater detail below. Rupturing the peelable seal can allow the contents of the chambers to safely mix without exposure to the environment or being contacted by a human. It should also be understood that one chamber can be larger than the other chamber(s) or each chamber can be of equal of substantially similar dimensions or volume.

In one application for the container 10, the upper compartment 17 is filled with a liquid diluent and the intermediate compartment 19 is filled with a medicament, such as an active pharmaceutical ingredient, or other nutritional or supplemental ingredient intended to be ingested by the user or patient and which can be provided in any form, including a liquid, gel, gas, or solid form. The lower compartment 20 can function as a security interface for an outlet port 30 and remains empty until the container is ready to be used. In this embodiment, the upper chamber 17 can contain a liquid diluent(s) while the intermediate chamber 19 can contain the medicament, active pharmaceutical ingredient (API), nutritional ingredient, or other supplemental ingredient, any of which can be either a dry powder, gel, solid or a liquid.

A procedure and apparatus for fabricating the container 10 of FIGS. 1 and 2 will now be described in connection with FIG. 3. Both the disclosed apparatus and procedure are adapted to be suitable for manufacturing containers with front and rear sheets having either single or multi-layer laminate films. Also, it should be understood that the number, shape, configuration and location of the container seals can be changed due to the modular arrangement of the components of FIG. 3.

Figure 3:
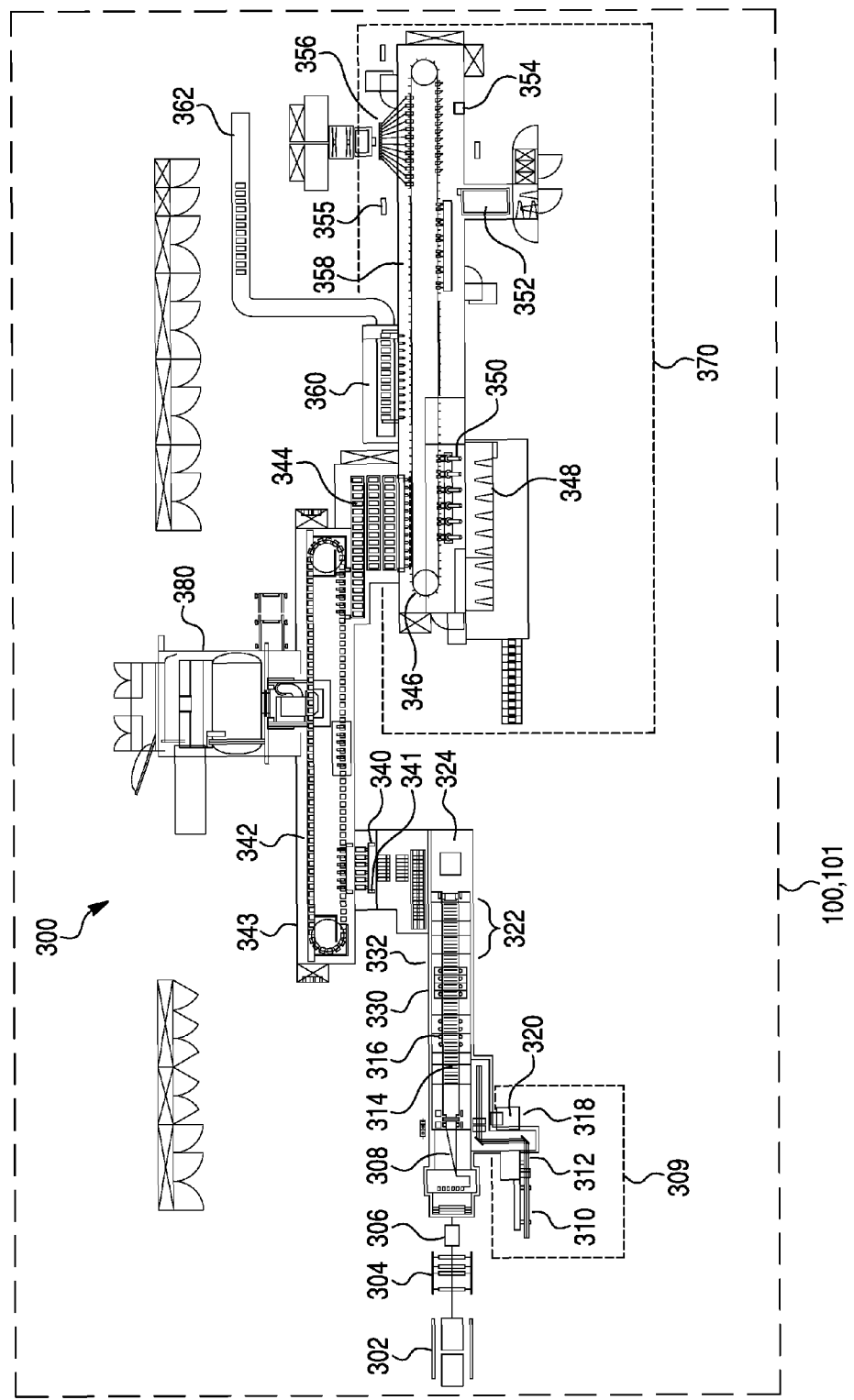
FIG. 3 is a diagrammatic plan view of an embodiment of a continuous, in-line container fabrication apparatus in accordance with the disclosed subject matter.
Figure 4A:
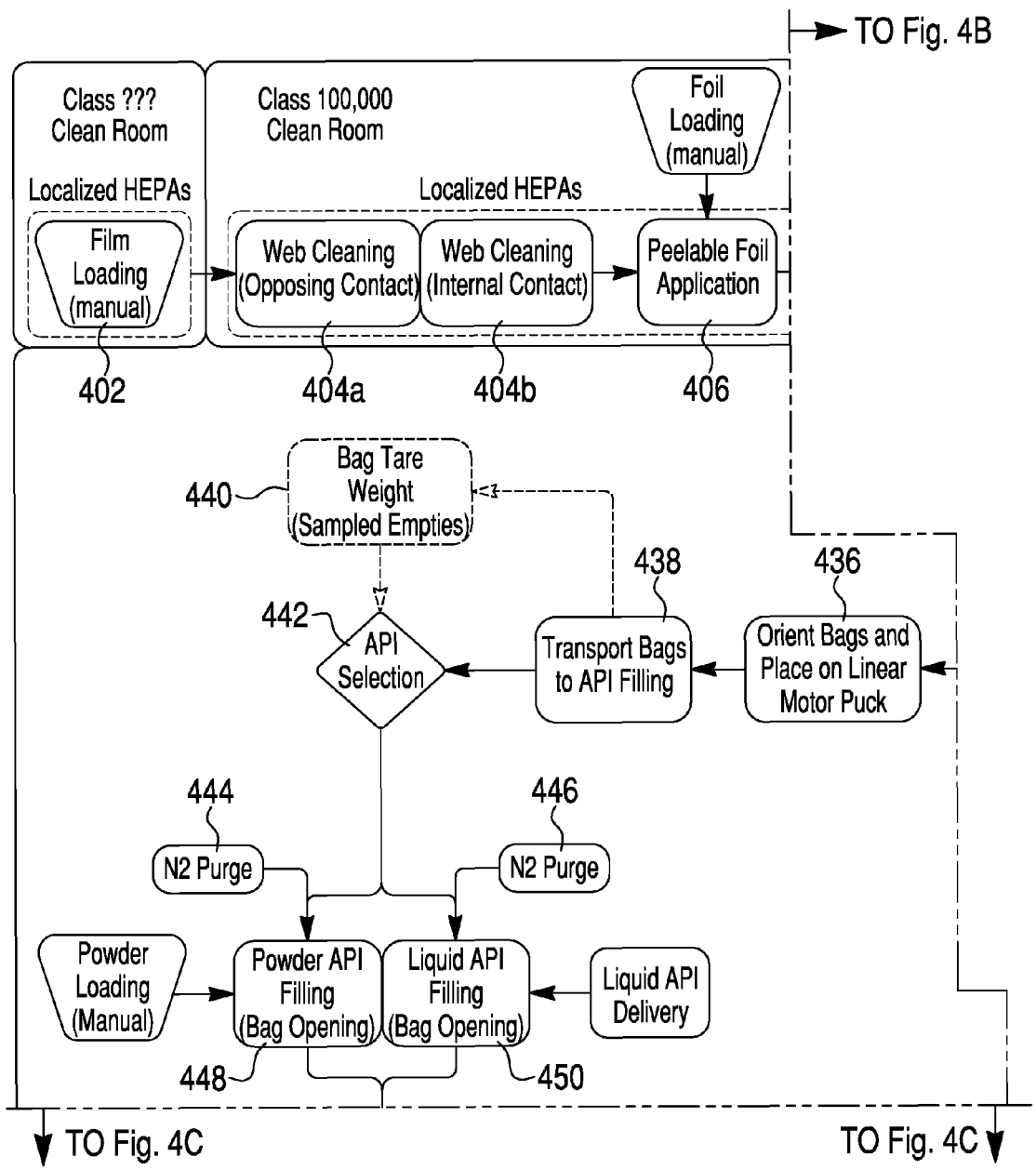
FIGS. 4A-D shows a flow chart of an exemplary process for manufacturing a container in accordance with principles of the disclosed subject matter.
Figure 4B:
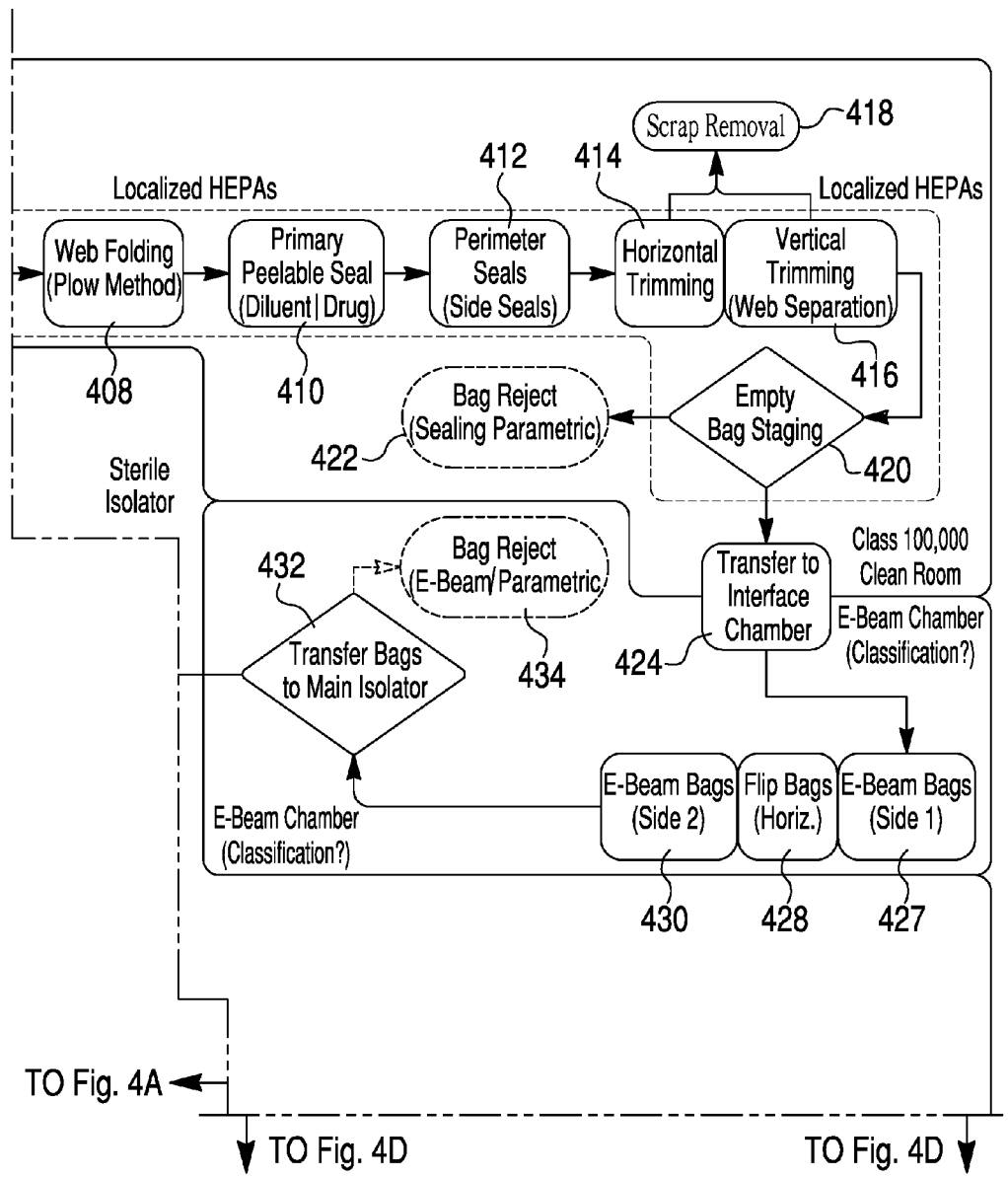
Figure 4C:
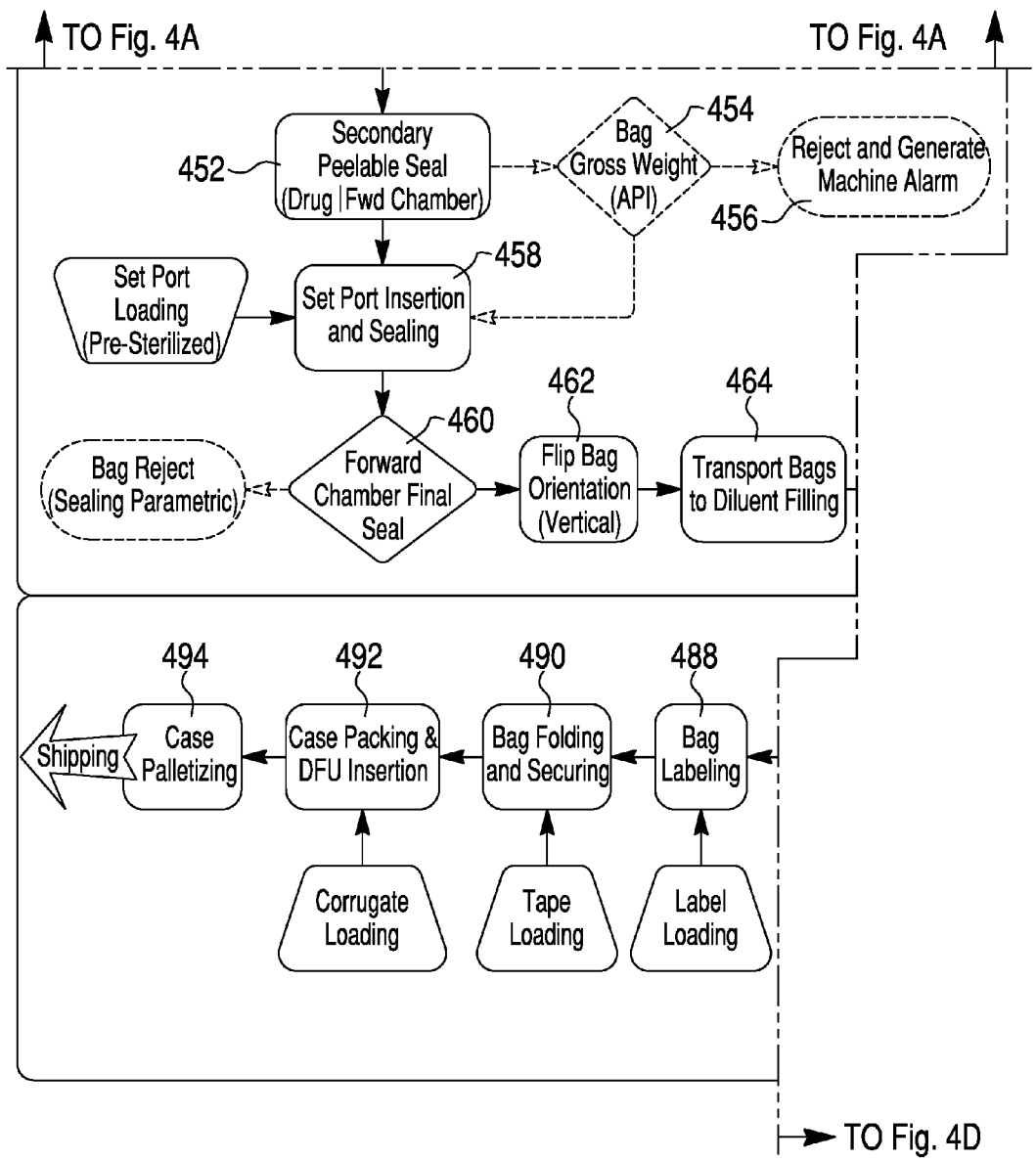
Figure 4D:
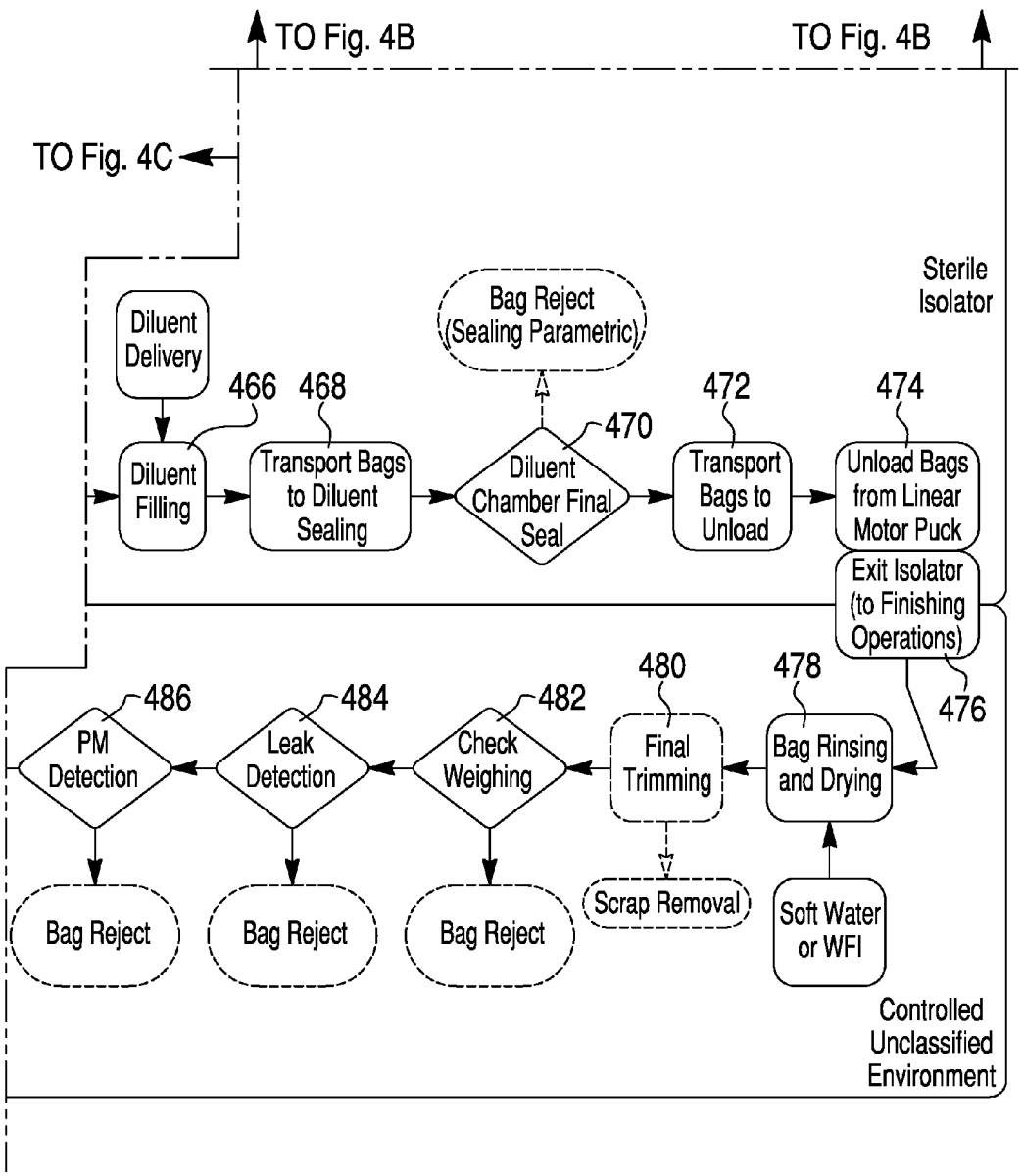

FIG. 3 is a semi-schematic plan view of an exemplary embodiment of a continuous, in-line container fabrication machine or system 300 showing the arrangement and positioning of various seal forming stations, primary film web supply rolls, e-beam irradiation stations, API loading stations, etc. FIG. 3 shows a bag roll film module 302 that provides bulk material for the container front and rear sheets. The bag roll module 302 is mounted at the intake end of the container fabrication machine 300 so that a primary bag film can be loaded onto the bag forming section of the production line. The film loading operations can be automated where appropriate in accordance with the rest of the line processes. A splicing mechanism (not shown) can be provided for continuous operation, and sufficient film accumulation can be provided to allow for appropriate roll changeover times. Visual guides, instructions or intuitive machine design for proper threading and loading of primary film rolls can be used. All mechanical aides desired for roll manipulation and handling should not interfere with the normal operation of the equipment. Tension and tracking of primary film roll can be controlled and monitored. All appropriate alarms, including but not limited to broken web or loss of tension, can be provided.

A film accumulator 304 receives the film from the bag film module 302 and feeds it to a cleaning roller 306 that cleans the films before they are shaped and formed into containers. For example, contact web cleaners and an ionized air supply can be maintained at the primary film loading station to maintain a clean environment with minimal particle accumulation onto the primary film roll. The web cleaners can be automatically monitored and can alert operators when periodic intervention is desired (i.e. adhesive paper changes).

The fabrication machine 300 can further include a module 309 in which the peelable foil is loaded onto the bag forming section of the production line. The module 309 includes a foil roll 310 and accumulator 312 that feeds the foil to a rotary die cutter 318 that is provided to cut the foil into the desired shape. At this stage, the peelable foil is slit/trimmed to its final configuration and transported for welding onto the primary film. The foil loading operations can be automated where appropriate in accordance with the rest of the line processes. A splicing mechanism can be provided for continuous operation. Sufficient foil accumulation can be provided to allow for appropriate roll changeover times. Visual guides, instructions or intuitive machine design for proper threading and loading of primary film rolls can be used. The module 309 may also include a component for alerting operators when a peelable foil roll is near exhaustion and operator intervention will be desired and can be implemented. All mechanical aides desired for roll manipulation and handling do not interfere with the normal operation of the equipment. Tension and tracking of peelable foil roll can be controlled and monitored. All appropriate alarms, including but not limited to broken web or loss of tension, can be provided. Trimming and separation of peelable foil can be continuously monitored for improper registration or improper final trim. Visual and audible alarms can be used to immediately alert the operators to take corrective action of any errors or deficiencies. Any trimming operations can be designed to minimize particular matter (PM) generation and prevent any PM from migrating onto the product. The module 309 can also include an automatic waste removal system 320.

The container fabrication machine 300 can also include a film folder 308 that folds the primary film to form a pouch that results in the flexible container. An alternative is to use two rolls of primary film and bring them together which may provide an easier method for maintaining alignment and avoiding jams. The primary film can be folded along the centerline of a primary web. Film orientation should be properly maintained at all times. In one embodiment, opposing peelable foil strips are maintained at an alignment within about +1.5 mm when brought together. Excessive film 'walk' can be monitored. Visual and audible alarms can be in place to alert operators when intervention is desired. Any web breaks, jams or loss of tension can be monitored. Appropriate alarms can be in place to alert operators when intervention is desired.

A trim station and foil welder 314 can also be provided. At this stage, the trimmed peelable foil can be sealed to the primary film web. The peelable foil can be properly registered and located on the primary film. Visual and audible alarms can be used to alert operators to any alignment issues requiring operator intervention. The location of the peelable foil welding tool can be adjustable and accommodate product configuration changes as necessary. All relevant process parameters such as temperature, pressure and dwell time can be continuously monitored and individually controlled at this station, either manually or automatically by a controller such as a CPU, PLC, or other. Visual and audible alarms can be used to alert operators to any process parameters out of specification. The system can be configured to compensate for machine stoppage and start conditions to avoid over-welding or under-welding the peelable foil to the primary container.

The machine 300 can also include a primary peelable sealing station 316. At this station, the machine 300 can be configured to automatically apply the primary peelable seal between the diluents and medicament/API chamber. The primary film can be properly registered and located at the peelable seal station. The peelable seal tooling can provide a minimum peelable seal width of, for example, 7 mm. All relevant process parameters such as temperature, pressure and dwell time can be monitored and individually controlled. Visual and audible alarms can be used to alert operators to any process parameters out of specification. A cooling station can be present and monitored as desired.

The machine 300 can also include a perimeter seal (side) welding station 330. At this station 330, the machine 300 will automatically apply the side perimeter seals on each container. The primary film can be properly registered and located at the peelable seal station 316. All relevant process parameters such as temperature, pressure and dwell time can be monitored and individually controlled. Visual and audible alarms can be used to alert operators to any process parameters out of specification. A cooling station 332 can be present and monitored as desired. If a cooling station is used, it can be designed to avoid condensation.

The machine also includes a cutting station 322 that may include a punching station, a corner cutting station and a side cutting station. The cutting station 322 automatically trims the edges of the containers and serves to open the folded side of the container. These stations can also determine the overall length of each flexible container. Location of trim blades can be properly marked and located for each of the different sized containers. If a heat knife is used, all relevant process parameters can be monitored. Any potential fumes caused by this process can be properly extracted. All waste generated can be automatically removed at station 324.

The formed containers now enter a bag transfer station 340 for transfer into an e-beam sterilization unit/e-beam generator 380 via conveyor structure 343. The bag transfer station 340 transfers individual (partially constructed) flexible containers onto an e-beam bag carrier (carrier device or carrier structure 342). This mechanism can accommodate each of the different sized containers. All bags not properly formed at previous stations can be rejected prior to transfer. The bag carrier 342 can be properly oriented and opened for receiving formed containers, as described above. Flexible containers can be properly positioned into the carrier mechanism and positive orientation can be maintained throughout the transfer process. The bag carrier 342 can be properly closed and latched as desired.

The bag carrier 342, which may also be referred to as a carriage, secures the formed containers or bags as they are processed through the e-beam equipment. In one embodiment, the carrier 342 will transport the formed containers through the e-beam process at a rate of 36 m/min. or an equivalent run rate of 60 bags per minute. The carrier device or structure 342 can also be configured to rotate 1800 (and possibly 360° or more, if desired) during the e-beam process in order to expose multiple sides of the formed bags to the sterilizing radiation while minimizing overexposure to the primary film. This rotation can be performed on the length axis of the bag. Alternatively, a shuttle mechanism 341 can be configured to rotate the bag during the e-beam process (180°, 360° or more, if desired). In one embodiment, the carrier device or structure 342 is configured so that the containers are mounted horizontally (flat) for e-beam processing. In another embodiment, the carrier device or structure 342 is configured so that the bags are mounted vertically for e-beam processing. Various embodiments of the carrier device or structure 342 are configured to move thorough a range of motion, including, but not limited to, rotation from 0 to 360 degrees about any one or all of the x, y and z axes, including but not limited to the longitudinal axis of the bag.

The e-beam sterilization chamber and process will now be described in more detail. The e-beam chamber provides sterilization for the formed flexible containers prior to final fill and forming and/or prior to entry into an isolator network for loading of the medicament/API. All relevant process parameters can be monitored. Visual and audible alarms can be used to alert operators to any process parameters out of specification. The bag carrier device or structure 342 can be configured to rotate 180 degrees during the process to equally expose both sides of the flexible container. This flip process can be properly monitored and operate in a fail-safe mode. Any container which does not positively register a rotation can be rejected. All sparking, arcing, voltage/current spikes or other process anomalies consistent with e-beam operation can be monitored and alarmed. If they occur, all containers affected during that cycle can be properly rejected. All safety precautions and machine guarding related to e-beam radiation, x-ray by-products and ozone by-products of the process shall be in place. Shielding shall be sufficient to prevent any radiation escape. It is contemplated that an ozone scrubber could be used in the exhaust system. The system provides for the ability to collect random samples of bags prior to the e-beam station, during normal production. This feature can be built in to the system. Collected bags with dosimeters can be provided off line a few days before dosimeter qualification studies. Bags can be made from recent production runs and from three separate lots, as desired. The system can be configured to have the ability to load dosimeter fitted bags prior to the e-beam station, process with e-beam, and collect irradiated bags. This can be built in to the system as a qualification mode or manual mode. This may not be done during normal production. However, the faster and easier this step is, the quicker the turnaround back to production. Sampling can occur after cleaning, but prior to decontamination. The system can have the ability to perform validation runs with dose delivery from 2 kGy to 60 kGy. Dose delivery can be accurate to +10% or 1 kGy, whichever is greater. The system can be configured to ensure no exposure to lead. In other words, lead shielding can be contained in stainless steel from which the system is constructed. The system can be configured with the ability to monitor conveyor speed, e-beam power consumption, pulse rates, and sparking. The system can also include a failsafe mode in the event of exceeding ozone level of 0.3 ppm in room or other emergency.

The machine also provides a container transfer module 344 for transferring the containers from the e-beam transport mechanism to a filling station and/or isolator 370. This module 344 transfers individual containers from the e-beam chamber for introduction into the filling station and/or isolator 370. Mechanism 344 can accommodate each of the different sized containers. The transport mechanism can be properly oriented and opened for removing containers from the e-beam chamber. The containers can be properly oriented and positioned into the staging area prior to entry into the filling station and/or isolator 370. The containers can be properly oriented and secured onto the main transport mechanism. The transfer process can be configured so as not to compromise sterility of the fill system and/or the main isolator network. In the embodiment of FIG. 3, the containers move within the filling station and/or isolator 370 in a counter clockwise direction.

The disclosed manufacturing system can include several mechanisms for opening the bag for filling the medicament/API chamber. In one embodiment, as shown in FIG. 3, an opening mechanism 346 uses actuated suction cups to separate the primary film prior to delivering powder or liquid into the chambers. Other embodiments for opening the bag or chambers include using clamps to separate the opposed laminate films, using gravity to separate the opposed laminate films, using directed or focused vibration energy to separate the opposed laminate films, using magnetic force to separate the opposed laminate films, using directed fluid to separate the opposed laminate films, etc.

The machine also includes an isolator 348 for filling the container with the medicament/API. Thus, once the laminate film or films have been opened or otherwise separated from each other, the chamber will be open and exposed and is ready to be filled. An injection nozzle can then be moved or directed toward the open end and caused to inject the medicament/API into the chamber through the opening. The opening is shaped to be large so as to minimize spillage and encourage expedited transfer of the fluid, thereby increasing speed of the overall process. A nitrogen wash can also be easily incorporated into the process immediately before filling of the medicament/API, etc. The wash process can also be quicker than is known in conventional flexible bag processes due to the relatively large opening in the upper chamber that receives (and removes) the nitrogen wash.

An embodiment of the medicament/API filling station/isolator 370 will now be described in more detail. This module is responsible for filling powdered medicament/API into the medicament/API chamber of the containers. Additionally, the construction of a secondary peelable seal can be performed at this station. The powder filling station can be designed to minimize or eliminate changeover parts. A powder level in each filling hopper can be continuously monitored and controlled. In the event the powder level of any individual hopper falls below minimum levels desired for maintaining an efficient filling process, audible and visual alarms can be used to alert operators to intervene. The offending hopper can be positively identified by the system controller. The powder fill weight targets delivered to each flexible container by the filling system can be individually controlled and changed through the HMI using appropriate security controls. The powder filling mechanism should be capable of accurately dispensing target powder fill weights within the following exemplary range and accuracy targets:

| Target Fill Weight (g) |
| --- |
| .05 |
| .50 |
| 1.00 |
| 2.00 |
| 4.00 |
| 8.00 |

The ability to periodically check the weight of the medicament/API being filled into the containers can be present. The powder medicament/API filling mechanism can be capable of receiving periodic feedback from the check weigh process and to adjust as necessary. All critical dosing process parameters can be continuously monitored as appropriate. These parameters may include servo load, auger rotation, wiper rotation, etc. The powder medicament/API dosing mechanism can provide a mechanism for minimizing potential product dusting. The fill line for the powdered medicament/API can be below the area where the secondary peelable seal will be located. Shielding mechanisms or filling nozzles may be used to prevent excess powder accumulation above the secondary peelable seal line. Construction of the secondary peelable seal can be performed immediately after powder dosing and at the same station. Movement of the container should be minimized prior to the application of the secondary peelable seal. The peelable seal tooling can provide a minimum peelable seal width of 7 mm. All relevant process parameters such as temperature, pressure and dwell time can be monitored and individually controlled. Visual and audible alarms can be used to alert operators to any process parameters out of specification.

The disclosed embodiments also contemplate a liquid medicament/API instead of a solid or powder. An exemplary liquid filling system module and process will now be described in greater detail. This module is responsible for filling liquid into a chamber of the containers. Additionally, the secondary peelable seal can be performed at this station. The liquid filling station can be designed to minimize or eliminate changeover parts. Filling nozzles can be designed to minimize drips. Any drips should not contaminate sealing surfaces. A liquid reservoir or surge tank can be incorporated to avoid starving the filling operation. The available liquid can be continuously monitored through an appropriate mechanism such as mass or volume. Audible and visual alarms can alert operators to low liquid levels when intervention is desired to avoid starving the filling equipment. The liquid volume delivered to each container by the filling system can be individually controlled and changed through the system using appropriate security controls. The liquid filling mechanism can be capable of providing continuous feedback on the volume of liquid delivered to each container. The properties of the liquid being dosed can be taken into account if using mass flow sensors for feedback. The ability to maintain standard recipes and verify the accuracy of the continuous feedback can be built into the system. The liquid filling mechanism can be capable of accurately dispensing target liquid volumes within the following range and accuracy targets:

| Target Fill Volume (cc) |
| --- |
| .50 |
| 1.0 |
| 3.0 |
| 6.0 |

The liquid dosing mechanism can provide a mechanism for minimizing liquid splashing and foaming. The fill line for the liquid can be below the area where the secondary peelable seal will be located. Shielding mechanisms or filling nozzles may be used to prevent excess liquid accumulation above the secondary peelable seal line. Construction of the secondary peelable seal should be performed immediately after liquid dosing at the same station. Movement of the container should be minimized prior to the application of the secondary peelable seal. The peelable seal tooling can provide a minimum peelable seal width of 7 mm. All relevant process parameters such as temperature, pressure and dwell time can be monitored and independently controlled. Visual and audible alarms shall be used to alert operators to any process parameters out of specification.

Next, the container is sealed at a peelable sealing station 350. The machine 300 also includes a port insertion and welding station 352 for installing the container outlet port. An exemplary port insertion and sealing station and process will now be described. This module is responsible for orienting the container setports in the container and permanently sealing the forward chamber. Individual ports can be properly oriented and staged. Setports or ports can be supplied to the isolator network in a non-oriented bulk package. The port insertion station and sealing mechanism may be able to minimize particulate matter (PM) generation and provide a mechanism for evacuating any PM generated due to normal port handling operations. One (1) setport can be accurately placed into the forward chamber of each container. The final location of the ports can comply with all applicable product drawings and specifications as provided. The setport can be permanently sealed to the container and any final welding operations completed. The final welds can be free of any functional defects such as leaks, wrinkles, bubbles, creases, or voids. Visual defects such as excessive scuffing or abrasion can be avoided. All relevant process parameters such as temperature, pressure and dwell time can be monitored and independently controlled. Visual and audible alarms can be used to alert operators to any process parameters out of specification.

A bag inversion module 354 is then provided which inverts the bags in preparation for liquid filling. Module 354 is responsible for orienting the container for diluent filling. The container can be oriented with the opening of the diluent chamber presented to the diluent filling station. Each container can be properly oriented and positively registered using a fail-safe mechanism. The rotation/inversion module 354 can be configured so as not to cause damage to any portion of the containers. Primary and secondary peelable seals can be protected from excessive force during the rotation process. Setports can be protected from any scratches, abrasion or marking. The integrity of the removable foil barriers should not be compromised. The process can be configured to avoid any introduction of particulate matter into the diluent chamber during processing. Shielding may be used as appropriate.

The container is then filled with a liquid, such as a diluent at a liquid filling station 356. As described on connection with the medicament/API filling isolator 348 above, the liquid filling station 356 can include nozzles for filling the containers with a diluent. An exemplary diluent filling system and process will now be described in greater detail. This module is responsible for filling diluent into the diluent chamber of the containers. The liquid filling station can be designed to minimize or eliminate changeover parts. The station can include the following features: filling nozzles designed to minimize drips and such that any drips do not contaminate sealing surfaces; and a liquid diluent reservoir or surge tank incorporated to avoid starving the filling operation. The available liquid diluent can be continuously monitored through appropriate means such as mass or volume sensors. Audible and visual alarms can alert operators to low liquid levels when intervention is desired to avoid starving the filling equipment. The liquid diluent volume delivered to each container can be individually controlled and changed through the system using appropriate security controls. The liquid diluent filling mechanism can be capable of providing continuous feedback on the volume of liquid delivered to each container. The properties of the liquid being delivered can be taken into account if using mass flow sensors for feedback. The ability to maintain standard recipes and verify the accuracy of the continuous feedback can be built into the system. The liquid filling mechanism can be capable of accurately dispensing target liquid volumes within the following range and accuracy targets:

| Target Fill Volume (mL) | Tolerance (mL) |
|---|---|
| 55.0 | ±2.0 |
| 108.0 | ±2.0 |
| 267.0 | ±2.0 |

The liquid diluent dosing mechanism can be configured to minimize liquid splashing and foaming. Shielding mechanisms or filling nozzles may be used as desired.

The containers then move to a sealing station 358 where a final seal is applied sealing top-most opening of the container after the diluent has been deposited in the diluent chamber of the flexible container. In one embodiment, the sealing station 358 is provided for completing the container perimeter seal on the diluent chamber. In this step, movement of the container should be minimized prior to the application of the final seal. In one embodiment, where processing time allows it, the final seal can be performed at the same station as diluent filling to avoid product movement and splashing. The container can be permanently sealed at this point. The final welds sealing the perimeter of the diluents chamber should be free of any functional defects such as leaks, wrinkles, bubbles, creases, or voids, as well as visual defects such as excessive scuffing or abrasion. The process for final bag sealing also includes monitoring and controlling of various process parameters, such as temperature, pressure and dwell time. In one embodiment, the process also includes visual and/or audible alarms used to alert operators to any process parameters out of specification. Any final trimming or hanger punch operations performed at this stage can be performed in a manner which minimizes particulate matter (PM) generation. The containers then move to a bag transfer station 360 for transfer along a conveyer 362 that prepares the containers for packaging.

The disclosed embodiments for manufacturing a flexible container include a process for removing the individual containers from the main transport mechanism and orienting the containers for exiting the isolator network. In this step of the process, the containers can be oriented and removed from the main transport mechanism without creating excessive stress on the container system. Care is taken to avoid any excessive abrasion, scuffing or marking on the primary container or setport. The orientation of the containers can be maintained as appropriate for exiting the isolator.

The flexible containers can exit the isolator in such a manner as to avoid any potential contamination from entering into the sterile isolator network. This can be facilitated by applying and maintaining positive pressure across any mouse-hole openings. All relevant process parameters such as temperature, pressure and dwell time can be monitored and independently controlled. Visual and audible alarms can be used to alert operators to any process parameters out of specification.

The disclosed embodiments for manufacturing a flexible container can also include process for performing factory acceptance testing at the supplier's facility to verify that the finishing line is acceptable and complies with desired specifications. The factory acceptance testing can include a documented examination of the equipment design and a determination of equipment calibration. Information obtained from this examination can be used to establish written procedures covering equipment setup, adjustment, calibration, maintenance, monitoring and control.

The factory acceptance testing also include the steps of: taking inventory of major components listed in the bills of materials submitted by the supplier; identifying desired equipment utilities, their sizes, pressures, flow rates, etc., and their hook-up locations; inspection of the material certification sheets provided for the system components; review of major component specifications to ensure compliance with this specification; review of component labeling; review of the documentation package; review of critical equipment or adjustments necessary to ensure proper operation of the equipment; and a "dry run" test without components performed for a predetermined duration.

One of the goals of the factory acceptance testing is to adequately determine if the machine can be made to satisfy the requirements of qualification testing (IQ/OQ/PQ) under actual operating conditions.

An embodiment of a main processing isolator and process will be described. This module encloses all aseptic processes and serves as the primary barrier to microbial contamination in the final product. The isolator enclosure can meet all ISO 5 Isolator requirements and can include the following: polycarbonate doors; 340 SS construction; access doors—positive seals/vacuum control or compression seals; glove ports; capable of aseptic removal/replacement of gloves; positive pressure cascade; cleanliness requirements; central drainage; air handling/air changes; and minimum volume/dead space.

A description of VHP compatibility will be described next. The system can have the following features: built in decontamination units; back-up capability—able to connect a portable unit in the event of failures of built-in unit; six log reduction vs. four log reduction; and aeration ppm targets.

An embodiment of a main transport mechanism will now be described in more detail. This module provides a main method for transporting the containers through the entire aseptic production process. This mechanism can include the ability to vertically rotate the container 1800 in order to present the container openings to the appropriate filling operation. The transport mechanism can be properly oriented and opened for receiving containers from the e-beam chamber. The transport mechanism can be designed to accommodate normal wear and tear that may occur over time. Normal wear and tear should not affect the overall accuracy and performance of the system provided regular scheduled maintenance is performed. The transport mechanism can be capable of handling all applicable container sizes. Changeover parts and tool changes can be minimized or eliminated as applicable. The location and orientation of each flexible container can be positively registered and controlled throughout the entire aseptic process. Container location and orientation can be positively identified and tracked for fail-safe operation and critical parameter controlled operations. Any container that cannot be positively identified can be considered a rejected container. Any container not positively identified as completing critical processing stages can also be rejected. The container may remain on the transport mechanism until the most appropriate reject location as long as it can be continuously tracked throughout the process. Otherwise, each container should be immediately removed from the transport mechanism. Products can be processed sequentially throughout the aseptic operation without diversion. The transport mechanism can be wash-down capable and designed to be decontaminated using a vaporous hydrogen peroxide process. Clean aseptic design can be applied to all features of the transport mechanism. The transport mechanism can be non-intrusive to each of the other critical aseptic processes. Any interference with other processing functions during normal operating conditions is not acceptable.

FIGS. 4A-D shows a process flow diagram illustrating the process for aseptically forming, filling, sealing and packaging a flexible container in accordance with one embodiment of the disclosed subject matter. The manufacturing concept for the flexible container system can include an integrated aseptic form, sterilize, fill, and seal process. FIGS. 4A-D shows an embodiment of a preliminary process flow diagram and equipment layout for the manufacturing of flexible containers in accordance with principles of the disclosed subject matter.

In FIGS. 4A-D, the process begins at step 402. In this step, the process of forming the container can take place in an ISO 8 (Class 100,000) clean room under localized HEPA filtration and deionization bars as necessary or desired. Rolls of primary film and aluminum barrier material are loaded onto forming equipment. Next, in step 404a and 404b, the opposing contact side and the internal contact side of the primary film can be cleaned using a contact roller system and accumulated through a series of rollers. In step 406, a peelable aluminum foil strip covering the API chamber can be trimmed to size and laminated in strips to the primary film with a removable weld. The foil can be loaded either manually or automatically at this step.

Next, in step 408, the film is folded and foil is die cut into two strips and routed to two different elevations, above and below the film. The foil is then cut to length and transferred to the container film and welded to both the top and bottom of the folded film.

The primary peelable seal which separates the diluent chamber from the drug chamber can be created in step 410. The primary peelable seal can be formed in a straight line perpendicular to both sides of the laminated films, or can be curved, zig-zag, or other shape. Next, in step 412, the folded primary film can then be sealed together along the length of the film to create the side perimeter seals. In another embodiment, the primary film can be aligned on top of a secondary film, and the two films can be welded or otherwise sealed along the length of each side. In another embodiment, the primary peelable seal is formed before the perimeter seal.

In step 414 and 416, the individual empty containers can then be trimmed and separated from the primary film roll and staged at step 420 for automatic loading into a sterile zone. Also, in one embodiment, at step 418, scrap from the trimming step can be mechanically removed from the process line.

At this point in time in the process, the flexible container is shaped with an upper chamber having a partially sealed perimeter with an opening formed in a top end of the upper chamber, and a lower chamber opposed to the upper chamber, the lower chamber similarly having a partially sealed perimeter but with an opening formed in a bottom end of the lower chamber. The upper chamber can be separated from the lower chamber by the primary peelable seal and the opening in the upper chamber can be diametrically opposed to the opening in the lower chamber. Thus, the laminated portion at this point in time can be formed in a substantial H-shape as viewed from a front of the partially constructed flexible container. Next, at step 422, the sealing qualities of the container can be evaluated and defective bags can be removed from the assembly line.

Next, in step 424, the flexible containers are transferred into an interface chamber which provides an interface between the container forming area of the production line and the e-beam chamber. At this step, in one embodiment, the partially constructed flexible container can be manipulated at this time such that the partially constructed flexible container is positioned in a vertical orientation (i.e, the opening in the upper chamber faces upward while the opening in the lower chamber faces downward). The manipulation can be achieved through the use of various controllers, such a central processing unit (CPU), server, personal computer (PC), programmable logic controlled (PLC) mechanisms, robotic elements, and other devices. The controller can be configured to provide directions and/or power to various mechanical devices to effect the desired manipulation of the partially constructed flexible container. For example, mechanical arms can be provided that include suction cups that can pick up the partially constructed flexible container and place it over a mandrel. The mandrel can include a pneumatic nozzle that delivers a quantity of fluid, such as Nitrogen gas, that will cause the opening in the lower chamber to expand such that it can be easily placed onto or over the mandrel. The mandrel can be built into a carrying tray or holder that will transport the partially constructed flexible container through subsequent steps of the manufacturing process. Alternatively, mechanical arms that include static electric charges, clamping structure(s), magnets, or other structures could be used to pick up and deliver the partially constructed flexible container to the mandrel or other holder device. Another alternative is to use cam or friction feeder bowl technology such that gravity or vibration moves the partially constructed flexible container from a first orientation to a second orientation such that a holder can deliver the partially constructed flexible container to a sterilization area.

Furthermore, at step 424, after bag forming, the partially constructed flexible container can be introduced into a sterilization area, such as a low-voltage (300 KeV) e-beam chamber, hydrogen peroxide wash, or other sterilization process area. The sterilization area can be located in the same clean room in which the partially constructed flexible container is formed. Thus, the partially constructed flexible containers are not desired to be moved to a separate facility or room and, instead, can remain "in-line" such that processing from the forming to the sterilization and back to filling can all take place in consecutive and sequential order if desired. This "in-line" process allows for much quicker manufacture of the flexible containers and allows for a higher degree of control of the sterile process (reducing opportunities for contamination and therefore reducing defects). Similarly, the disclosed "in-line" process can significantly reduce the cost associated with removing the partially constructed flexible containers from a first or "forming" clean room and transporting the partially constructed flexible container to a second "sterilization" or "e-beam" clean room, and then either redelivering or delivering back to the first or other clean room for the partially constructed flexible containers to be filled and finally formed or sealed.

As described above, each the partially constructed flexible containers can be automatically placed into a continuous transport system that delivers the partially constructed flexible containers to a sterilization process, such as e-beam sterilization. In particular, manipulation equipment, software and/or hardware can be provided to orient the partially constructed flexible containers for proper exposure to the e-beam emitter. Alternately, the flexible containers can be placed in an intermittent/index transport system.

In the embodiment of FIGS. 4A-D, at step 427, a first side of the bag is irradiated, then at step 428, the bag is flipped. Next, in step 430, a second side of the bag is irradiated.

The transport system for transporting the bags can include a 180° rotation mechanism to ensure complete penetration of the e-beam radiation into the partially constructed flexible container through only a single pass. In one embodiment, suitable shielding can be incorporated into the transport mechanism or holder to ensure portions of the partially constructed flexible container are blocked from irradiation from the e-beam such that portions of the partially constructed flexible containers are not overexposed to the e-beam. For example, if the entire front of the partially formed container is exposed to the irradiation from the e-beam, the diluents(s) and buffer chambers of the back of the partially formed container are shielded from the irradiation, such that the API chamber is the sole portion of the partially formed container that is exposed to the e-beam irradiation from the back side. The carrier system can continuously transport the individual containers through the low-voltage e-beam chamber at a constant speed to ensure they receive the proper e-beam dose to meet the desired sterility assurance level.

In another embodiment, the carrier system can include a single e-beam mechanism including two windows that are used to irradiate two sides of the container. In this embodiment, one side of the container is irradiated and then the container is flipped 180 degrees prior to exposure to the second window. In another embodiment, multiple e-beam mechanisms are provided. For example, the partially constructed flexible containers can pass in front of first and second e-beam mechanisms either simultaneously or in sequence to perform a desired sterilization process. When simultaneous, the e-beam devices can face each other. Alternatively, the e-beam devices can be spaced from each other and located on either side of the carrier system line. The first and/or second e-beam mechanisms can be provided with shielding mechanisms or be oriented or targeted in such a way to avoid overexposure of the partially constructed flexible containers in a similar manner as described above. Of course, additional e-beam devices can be added along the carrier system line, and can be directed as desired. Moreover, alternative arrangements of shielding can be provided to prevent overexposure to the diluents(s) and buffer chambers of the partially formed container.

Once the partially constructed flexible containers are sterilized, they are transported at step 432 to a main isolator for filling, for example, to an ISO 5 (Class 100) isolator. At optional step 434, each bag can be inspected to determine whether it was properly irradiated. Improperly irradiated bags can be taken off-line as rejected bags. Alternatively, the entire process of manufacturing the flexible containers can be accomplished within an isolator. In any case, each of the above-described process steps can take place in the same clean room to avoid the cost, time and possible production errors associated with transporting the flexible containers outside of a clean room during manufacture.

Regarding the above-referenced e-beam sterilization process, an evaluation of voltage dose mapping was performed in order to provide information about container 'hot' and 'cold' spots related to e-beam radiation exposure. The minimum e-beam dose was set at 18 kGy based on expected bio-burden levels while the maximum allowable e-beam dose was determined based on functional tests for container integrity. Exposure to e-beam radiation above 70 kGy can have an impact on plastic properties, particularly polypropylene and PET.

After sterilization, at step 436, the partially constructed flexible containers can then be placed onto a motorized system, such as an intermittent fixed link chain system or a linear motor puck system which will transport each partially constructed flexible container individually through the filling and sealing process. As described above, the empty (partially constructed) flexible containers can be oriented onto the linear motor pucks with the opening of the API/medicament chamber facing upward. The empty containers can then be transported at step 438 to the drug dosing system where the medicament or API is dosed into the drug/upper chamber. In optional step 440, the container can be weighed prior to being filled with the medicament/API. At step 442, the medicament/API is selected. The medicament/API can be in various forms, including powder form, gel, liquid form, capsule, tablet, combinations thereof, etc. For example, in step 450, a bulk sterile powder medicament/API can be supplied to an auger filling system through a standard aseptic transfer port system. Alternatively, in step 448, a sterile liquid medicament/API can be supplied to mass flow pumps through a series of sterile filter banks. The medicament/API can be delivered directly through the relatively wide opening in the medicament/API chamber which can reduce the amount of spillage and allow more accurate and quicker fill rates. As shown in FIGS. 4A-D, an $N_2$ purge may be applied to the bags prior to filling with the medicament/API. Also filling of the powder or liquid API can occur either manually or mechanically.

In step 452, a secondary peelable seal that separates the drug chamber from the forward or buffer chamber can be created after medicament/API filling. In step 454, the containers can be weighed after medicament/API filling to verify proper fill weights. For liquid medicament/API filling, mass flow pumps can be provided that provide continuous feedback of fill volume.

Next, at step 458, the containers are then transported to the setport insertion station where the setports are automatically inserted into the forward or buffer chamber and a closing seal is created on the setport. The setport can be pre-sterilized. At this point, at step 460, the lower end of the flexible container is fully formed by the peripheral seals enclosing this portion of the container. Optionally, the bags can also be inspected at this stage of the process and defective bags can be removed from the process line.

Next, in step 462, the containers can then be rotated 180° (or other angle) to orient the opening of the diluent chamber upward and the containers are transported at step 464 to a diluent filling station. Rotation can be accomplished in various manners, including use of feeder or vibration bowl technology, use of gravity to allow the partially constructed flexible container to "fall" over an obstacle 355 (the filled API chamber will be filled and heavier than the diluent chamber) and be "caught" by a holder cup or holding structure, use of mechanical arms with clamps, magnets, static electricity, suction cups or other holding manipulating devices that would allow the mechanical arm structure to rotate the partially constructed flexible container over a widthwise or horizontal axis of the container. Of course, similar technology could be incorporated directly into the holder or puck that is transporting the partially constructed flexible containers.

Additionally, the holder or pucks could be directly manipulated by the various methods and technology described above (instead of direct handling of the partially constructed flexible containers). Thus, the holder, puck, or conveyor belt itself, (conveyor 362), could "flip" over to allow for filling of the diluent chamber after the medicament/API is filled and the setport is installed. It should also be understood that the process for making and inserting the setport and final seal can be performed simultaneously or separately.

Diluent is then dosed at step 466 into the containers through a sterile filter bank using mass flow pumps and then at step 468, the containers are transported for diluent sealing. At step 470, the container is indexed to the next station where a final diluent seal is created. The containers are then transported to an unload station at step 472 where they will be removed from the motorized system and oriented for proper removal from the isolator network at step 474.

At step 476, the container exits the isolator for various "finishing operations." For example, at step 478, the containers are rinsed and dried. Then final trimming of the bag occurs at step 480 whereby scraps are removed from the production line. A series of tests are then conducted, including a weight check at step 482, a leak detection test at 484, and a PM detection test at 486. Containers that fail any of these tests are rejected and removed from the production line.

Next, the bags can be labeled at step 488, folded and secured at step 490 and packaged in containers at step 492. Finally, at step 494, each package containing multiple containers can be palletized for transport.

The disclosed process for manufacturing the flexible containers is lower in cost as compared to conventional manufacturing techniques through the elimination of waste in both material components and processing. In one embodiment, the manufacturing process involves just three primary components (primary film, peelable foil, and setport). Furthermore, the disclosed manufacturing process eliminates waste in processing and handling by consolidating the manufacturing into a single integrated in-line process which includes: bag forming, in-line e-beam sterilization, bag filling, and final sealing including setports. Further unit cost reduction is achieved through the increased output capacity of the disclosed manufacturing process.

While the subject matter has been described in detail with reference to exemplary embodiments thereof, it will be apparent to one skilled in the art that various changes can be made, and equivalents employed, without departing from the scope of the disclosure.

What is claimed is:

1. A system for manufacturing a flexible bag, comprising:
a single contained environment configured for aseptic processing;
a flexible bag forming station configured to form a flexible bag and located within the contained environment;
an e-beam sterilization station configured to sterilize the flexible bag and located within the single contained environment;
a conveyor structure for moving a carrier device and the flexible bag through the e-beam sterilization station in a first direction; and
a fill station configured to fill the flexible bag with at least two different materials, the fill station located within the single contained environment, wherein
the carrier device is configured to rotate the flexible bag about a first axis that is vertical relative to the first direction of the conveyor as the flexible bag travels through the e-beam sterilization station, and
the carrier device is configured to rotate the flexible bag about a second axis that is transverse relative to the first axis and relative to the first direction as the bag travels through the fill station.

2. The system of claim 1, further comprising:
a packaging station configured to unload the flexible bag after the flexible bag is filled with the at least two different materials, the packaging station located within the single contained environment.

3. The system of claim 1,
wherein the fill station is configured to fill a first portion of the flexible bag with a first of the at least two different materials prior to rotation of the flexible bag about the second axis and to fill a second portion of the flexible bag different from the first portion of the flexible bag with a second of the at least two different materials after rotation of the flexible bag about the second axis.

4. The system according to claim 3, wherein the flexible bag forming station is configured to form a peelable seal between the first portion of the flexible bag and the second portion of the flexible bag.

5. The system of claim 1, wherein
the e-beam sterilization station includes a single e-beam generator; and
the carrier device is configured to rotate the flexible bag about the first axis such that at least two opposing sides of the flexible bag are exposed to the single e-beam generator.

6. The system of claim 1, wherein:
the fill station is configured to fill a first portion of the flexible bag with a first fluid, and to fill a second portion of the flexible bag with at least one of a second fluid that is different from the first fluid and a powder.

7. The system of claim 1, wherein
the two different materials include at least one active pharmaceutical ingredient.

8. The system for manufacturing a flexible bag according to claim 1, wherein the second axis is horizontal relative to the first direction.

9. A method for manufacturing a flexible bag, comprising:
forming a flexible bag at a flexible bag forming station;
placing the flexible bag onto a carrier structure after forming the flexible bag;
moving the carrier structure and flexible bag through an e-beam sterilization station to sterilize the flexible bag;
providing a conveyor structure for moving the carrier structure and flexible bag through the e-beam sterilization station;
rotating the flexible bag about a first axis that is vertical relative to a first direction of the conveyor as the flexible bag travels through the e-beam sterilization station;
rotating the flexible bag about a second axis that is transverse relative to the first axis and relative to the first direction; and
filling the flexible bag at a fill station with at least two different materials after moving the carrier structure and flexible bag through the e-beam sterilization station.

10. The method of claim 9, wherein
the flexible bag includes a first portion for holding a first material, a second portion for holding a second material different from the first material, and a seal located between the first portion and second portion, and including the step of shielding at least a portion of the flexible bag from irradiation during the moving of the flexible bag through the e-beam sterilization station.

11. The method of claim 9, further comprising rotating the flexible bag using the carrier structure.

12. The method of claim 11, further comprising rotating the flexible bag using the carrier structure such that more than one side of the flexible bag is sterilized by an e-beam generator.

13. The method of claim 9, further comprising:
shielding at least a portion of the flexible bag from irradiation during the moving of the flexible bag through the e-beam sterilization station,
wherein the forming, placing, moving and filling all occur within a same and single contained environment.

14. The method of claim 9, further comprising:
transporting the flexible bag directly from the flexible bag forming station to the e-beam sterilization station and then directly to the fill station, wherein
each of the flexible bag forming station, the e-beam sterilization station, and the fill station are located within a same and single aseptic environment such that no environmentally separate transfer structure is used to move the flexible bag to and from the e-beam sterilization station.

15. The method of claim 9, further comprising:
transporting the flexible bag directly from the flexible bag forming station to the e-beam sterilization station and then directly to the fill station using only automated mechanical structures.

16. A system for manufacturing a filled flexible container, comprising:
a flexible container forming station configured to form a flexible container;
an e-beam sterilization station configured to sterilize the flexible container;
a fill station configured to fill the flexible container with at least two different materials, including a first material and a second material;
a first conveyor directly connecting the flexible container manufacturing station to the e-beam sterilization station;
a second conveyor directly connecting the e-beam sterilization station to the fill station, and
a carrier device configured to rotate the flexible container about a first axis that is vertical to a direction of the first conveyor as the flexible container travels through the e-beam sterilization station, and
the carrier device is configured to rotate the flexible container about a second axis that is transverse relative to the first axis and to the direction of the first conveyor prior to filling of the flexible container with the second material.

17. The system of claim 16, wherein
the flexible container forming station, the e-beam sterilization station, the fill station, the first conveyor, and the second conveyor are all located within a same single aseptic environment enclosure.

18. The system of claim 16,
wherein the carrier device is further configured to hold the flexible container as the flexible container travels through the e-beam sterilization station and to rotate the flexible container such that at least two opposing sides of the flexible container are exposed to an e-beam generator located in the e-beam sterilization station.

19. The system of claim 16, wherein the fill station is configured to fill the flexible container with the first material of the at least two different materials prior to rotating the flexible container about the second axis, and to fill the flexible container with the second material of the at least two different materials after rotating the flexible container about the second axis.

20. The system of claim 19, wherein the first material is an active pharmaceutical ingredient and the second material is a diluent, and the flexible container manufacturing station is configured to form a peelable seal that separates the active pharmaceutical ingredient from the diluent.

21. The system of claim 16, wherein the carrier device includes an obstacle configured to rotate the flexible container about the second axis by means of gravity.

* * * * *